US006780428B2

(12) United States Patent
Ranger et al.

(10) Patent No.: US 6,780,428 B2
(45) Date of Patent: Aug. 24, 2004

(54) UNIMOLECULAR POLYMERIC MICELLES WITH AN IONIZABLE INNER CORE

(75) Inventors: Maxime Ranger, Rigaud (CA); Jean-Christophe Leroux, Montreal (CA)

(73) Assignee: Labopharm, Inc., Quebec (CA)

( * ) Notice: Subject to any disclaimer, the term of this patent is extended or adjusted under 35 U.S.C. 154(b) by 25 days.

(21) Appl. No.: 09/878,115

(22) Filed: Jun. 8, 2001

(65) Prior Publication Data

US 2002/0187199 A1 Dec. 12, 2002

(51) Int. Cl.$^7$ ............................................. A61K 1/127
(52) U.S. Cl. ........................... 424/450; 424/468; 514/2; 514/44
(58) Field of Search ................................. 424/450, 468, 424/490, 98.08; 514/2, 44; 435/320.1, 455

(56) References Cited

U.S. PATENT DOCUMENTS

| | | | |
|---|---|---|---|
| 5,041,516 A | | 8/1991 | Frechet et al. |
| 5,154,853 A | * | 10/1992 | Newkome .................. 252/311 |
| 5,206,410 A | | 4/1993 | Newkome et al. |
| 5,714,166 A | | 2/1998 | Tomalia et al. |
| 5,770,627 A | | 6/1998 | Inoue et al. |
| 5,788,989 A | | 8/1998 | Jansen et al. |
| 5,955,509 A | | 9/1999 | Webber et al. |
| 6,130,209 A | | 10/2000 | Newkome et al. |
| 6,177,414 B1 | | 1/2001 | Tomalia et al. |
| 6,312,727 B1 | * | 11/2001 | Schacht .................... 424/490 |
| 6,338,859 B1 | * | 1/2002 | Leroux ...................... 424/489 |
| 6,383,500 B1 | * | 5/2002 | Wooley ..................... 424/401 |
| 6,440,743 B1 | * | 8/2002 | Kabanov .................... 435/458 |
| 2003/0059398 A1 | * | 3/2003 | Ranger .................... 424/78.08 |

FOREIGN PATENT DOCUMENTS

| | | |
|---|---|---|
| WO | WO 01/87227 | 11/2001 |

OTHER PUBLICATIONS

Jones et al., Polymeric micelles —a new generation of colloidal drug carriers, Eur. J. Pharmaceut. Biopharmaceut., (1999) 48, pp.101–111.

Kwon et al., Polymeric micelles as new drug carriers, Adv. Drug Deliv. Rev., (1996) 21, pp107–116.

Allen et al., Nano —engineering block copolymer aggregates for drug delivery, Colloids Surf. B, (1999) 16, pp3–27.

Zhao et al., Fluorescence probe techniques used to study micelle formation in water–soluble block copolymers, Langmuir, (1990) 6, pp514–516.

Kabanov et al., The neuroleptic activity of haloperidol increases after its solubilization in surfactant micelles: Micelles as microcontainers for drug targeting, FEBS, (1989) 258, 2, pp343–345.

Zhang et al., Multiple morphologies of "crew –cut" aggregates of polystyrene –b– poly (acrylic acid), Science,(1995), 268, pp1728–1731.

Inoue et al., An AB block copolymer of oligo(methyl methacrylate) and poly(acrylic acid) for micellar delivery of hydrophobic drugs, J. Controlled Release, (1998) 51, pp221–229.

(List continued on next page.)

*Primary Examiner*—Dave Trong Nguyen
(74) *Attorney, Agent, or Firm*—McHale & Slavin, P.A.

(57) ABSTRACT

The present invention describes the preparation of unimolecular polymeric micelles (UPM) that bear a hydrophilic shell and a potentially ionizable and relatively hydrophobic core at a determined pH value. The core becomes electrostatically charged as the pH is changed. Such micelles can be made from either biodegradable or non-biodegradable polymers. Loaded drugs can be physically retained in the micelles when the pH of the surrounding medium favors interactions with the core. Upon a change in pH, modification in the ionization state of the core will decrease the interactions between the drug and the inner core and facilitate the release of the micellar contents.

9 Claims, 4 Drawing Sheets

The synthesis scheme of a UPM, with an ionizable and hydrophobized inner core, and a non-ionic hydrophilic outer shell.

OTHER PUBLICATIONS

Kataoka, Design of nanoscopic vehicles for drug targeting based on micellization of amphiphilic block copolymers, J. Macromol. Sci. —Pure Appl. Chem., (1994) A31, 11, pp1759–1769.

Kataoka et al., Doxorubicin–loaded poly(ethylene glycol)–poly(β–benzyl–L–aspartate) copolymer micelles: their pharmaceutical characteristics and biological significance, J. Controlled Release, (2000) 64, pp143–153.

Benahmed et al., Novel polymeric micelles based on the amphiphilic diblock copolymer poly(N–vinyl–2–pyrrolidone)–block–poly(D,L–lactide), Pharmaceut. Res., (2001) 18, 3, pp323–328.

Lee et al., Synthesis and micellar characterization of amphiphilic diblock copolymers based on poly(2–ethyl–2–oxazoline) and aliphatic polyesters, Macromol., (1999) 32, pp1847–1852.

Scholz et al., A novel reactive polymeric micelle with aldehyde groups on its surface, Macromol., (1995) 28, pp7295–7297.

Liu et al., Unimolecular micelles: Synthesis and characterization of amphiphilic polymer systems, J. Polymer Sci.: Part A: Polymer Chem., (1999) 37, pp703–711.

Liu et al., Water–soluble dendritic unimolecular micelles: Their potential as drug delivery agents, J. Controlled Release, (2000) 65, pp121–131.

Liu et al., Drug release characteristics of unimolecular polymeric micelles, J. Controlled Release, (2000), 68, pp167–174.

Ranger et al., Towards novel unimolecular polymeric micelles bearing an ionizable inner core for pH–controlled drug release, 28th Int. Symposium on Controlled Release of Bioactive Materials (2001).

Leroux, et al., "N–isopropylacrylamide copolymers for the preparation of pH–sensitive liposomes and polymeric micelles", J. Of Controlled Release (2001), vol. 72, No. 1–3, pp. 71–84.

Meyer, et al., "Copolymers of N–isopropylacrylamide can trigger pH sensitivity to stable liposomes", FEBS Letters, Elsevier Science Publishers (1998), vol. 421, No. 1, pp. 61–64.

* cited by examiner

The synthesis scheme of a UPM, with an ionizable and hydrophobized inner core, and a non-ionic hydrophilic outer shell.

$^1$H NMR spectrum of the tetrainitiator of the atom transfer radical polymerisation (ATRP).

$^1$H NMR spectra of the non-ionic
star-P(PEGMA200)-b-P(EMA$_{50}$-co-tBMA$_{50}$)

$^1$H NMR spectra of the ionizable star-P(PEGMA200)-b-P(EMA$_{50}$-co-MAA$_{50}$)

UNIMOLECULAR POLYMERIC MICELLES WITH AN IONIZABLE INNER CORE

FIELD OF THE INVENTION

This invention relates generally to the field of unimolecular polymeric micelles (UPM); particularly to UPM and their methods of preparation which result in a micelle having an ionizable core; and most particularly to the use of such micelles as carriers for pharmacological constituents; wherein a directed release of said constituents in response to the ionization state induced upon the UPM is realized.

BACKGROUND OF THE INVENTION

In order to improve the specific delivery of drugs with a low therapeutic index, several drug carriers such as liposomes, microparticles, nano-associates (e.g. polymeric micelles, polyion complex micelles (PICM)) and drug-polymer conjugates have been studied. In recent years, water-soluble supramolecular assemblies such as polymeric micelles and PICM have emerged as promising new colloidal carriers for the delivery of hydrophobic drugs and polyions (e.g. antisense oligonucleotides), respectively.

Polymeric micelles have been the object of growing scientific attention, and have emerged as potential carriers for drugs having poor water solubility because they can solubilize those drugs in their inner core and they offer attractive characteristics such as a generally small size (<300 nm) and a propensity to evade scavenging by the mononuclear phagocyte system.

Micelles are often compared to naturally occurring carriers such as viruses or lipoproteins. All three of these carriers demonstrate a similar core-shell structure that allows for their contents to be protected during transportation to the target cell, whether it is DNA for viruses or water-insoluble drugs for lipoproteins and micelles.

Polymeric micelles seem to be one of the most advantageous carriers for the delivery of poorly water-soluble drugs as reported by Jones and Leroux, *Eur. J. Pharm. Biopharm.* (1999) 48, 101–111; Kwon and Okano, *Adv. Drug Deliv. Rev.* (1996) 21, 107–116 and Allen et al. *Colloids Surf. B: Biointerf.* (1999) 16, 3–27. They are characterized by a core-shell structure. The hydrophobic inner core generally serves as a microenvironment for the solubilization of poorly water-soluble drugs, whereas the hydrophilic outer shell is responsible for micelle stability, protection against opsonization, and uptake by the mononuclear phagocyte system. Pharmaceutical research on polymeric micelles has been mainly focused on copolymers having an AB diblock structure with A, the hydrophilic shell moieties and B the hydrophobic core polymers, respectively. Multiblock copolymers such as poly(ethylene oxide)-poly(propyleneoxide)-poly(ethylene oxide) (PEO-PPO-PEO) (A-B-A) can also self-organize into micelles, and have been described as potential drug carriers. E.g. Kabanov et al., *FEBBS Lett.* (1989) 258, 343–345. The hydrophobic core which generally consists of a biodegradable polymer such as a poly(β-benzyl-aspartate) (PBLA), poly(D,L-lactic acid) or poly(ε-caprolactone), serves as a reservoir for a poorly water-soluble drug, protecting it from contact with the aqueous environment. The core may also consist of a water-soluble polymer, such as poly(aspartic acid) (P(Asp)), which is rendered hydrophobic by the chemical conjugation of a hydrophobic drug, or is formed through the association of two oppositely charged polyions (PICM). Several studies also describe the use of poorly or non-biodegradable polymers, such as polystyrene (PSt) or poly(methyl methacrylate)(PMMA), as constituents of the inner core. See, e.g., Zhao et al., *Langmuir* (1990) 6, 514–516; Zhang et al., *Science* (1995) 268, 1728–1731; Inoue et al., *J. Controlled Release* (1998) 51, 221–229 and Kataoka J. *Macromol. Sci. Pure Appl. Chem.* (1994) A31, 1759–1769. The hydrophobic inner core can also consist of a highly hydrophobic small chain such as an alkyl chain or a diacyl-lipid (e.g. distearoyl phosphatidyl ethanolamine). The hydrophobic chain can be either attached to one end of a polymer, or randomly distributed within the polymeric structure. The shell usually consists of chains of hydrophilic, non-biodegradable, biocompatible polymers such as poly (ethylene oxide) (PEO) (see Allen et al. *Colloids Surf. B: Biointerf.* (1999) 16, 3–27 and Kataoka et al. *J. Controlled Release* (2000) 64, 143–153), poly(N-vinyl-2-pyrrolidone) (PVP) (see Benahmed A et al. *Pharm Res* (2001) 18, 323–328) or poly(2ethyl-2-oxazoline) (see Lee et al. *Macromolecules* (1999) 32, 1847–1852). The biodistribution of the carrier is mainly dictated by the nature of the hydrophilic shell. Other polymers such as poly(N-isopropylacrylamide) and poly(alkylacrylic acid) impart temperature or pH sensitivity to the micelles, and could eventually be used to confer bioadhesive properties (see U.S. Pat. No. 5,770,627). Micelles presenting functional groups at their surface for conjugation with a targeting moiety have also been described (See, e.g., Scholz, C. et al., *Macromolecules* (1995) 28, 7295–7297).

Unimolecular polymeric micelles (UPM) consist of a single macromolecule having an inner core and an outer shell which differ in their hydrophobic and hydrophilic character (see Liu et al. *J. Polym. Sci. Part A: Polym. Chem.* (1999) 37, 703–711; Liu et al. *J. Controlled Release* (2000) 65, 121–131). In drug delivery, unimolecular polymeric micelles possess generally a hydrophobic core and a hydrophilic corona. As opposed to supramolecular assemblies, unimolecular micelles are intrinsically stable because they do not show any critical association concentration (CAC per se). Such micelles can solubilize poorly water-soluble compounds and be used as carriers for drug targeting. Since unimolecular micelles do not dissociate upon dilution, compounds are usually released from the inner core by diffusion and/or following the degradation of the polymer backbone (see Liu et al. *J. Controlled Release* (2000) 68, 167–171). In the case of non biodegradable unimolecular micelles, diffusion is the sole mechanism of drug release.

What is therefore lacking in the prior art is a UPM which is designed to have a more elegant means for release of their contents. More specifically, if a UPM was synthesized with an ionizable inner core, it could be useful in a variety of pharmaceutical applications. For instance, micelles intended to be administered by the oral route can be designed to have a core bearing carboxylic acid groups. Hydrophobic or substantially hydrophobic drugs will be loaded in the inner core under conditions where the latter is protonated. Such micelles should release their contents in the small intestine as the pH rises.

DESCRIPTION OF THE PRIOR ART

U.S. Pat. No. 5,714,166 discloses dendritic polymer conjugates which are composed of at least one dendrimer in association with at least one unit of a carried material, where the carrier material can be a biological response modifier, have been prepared. The conjugate can also have a target director present, and when it is present then the carried material may be a bioactive agent. Preferred dendritic polymers are dense star polymers, which have been complexed with biological response modifiers. These conjugates and complexes have particularly advantageous properties due to their unique characteristics.

U.S. Pat. No. 6,177,414 is directed toward starburst conjugates which are composed of at least one dendrimer in association with at least one unit of a carried agricultural, pharmaceutical, or other material. These conjugates have particularly advantageous properties due to the unique characteristics of the dendrimer. The carried material is salicylic acid and the dendrimer polymer is a polyamidoamine.

U.S. Pat. No. 6,130,209 relates a key micelle molecule comprising a core molecule and a plurality of branches extending therefrom, at least one of said branches including a shank portion extending therefrom having a terminal moiety at an end thereof providing a secondary and tertiary structure allowing entrance into a void region of a lock micelle for binding to a complementary acceptor within the void region of the lock unimolecular micelle.

U.S. Pat. No. 5,154,853 cites a method of making a cascade polymer, which includes the steps of: alkylating the branches of a multi-branched core alkyl compound with a terminal alkyne building block including multiple ethereal side chains, and simultaneously reducing the alkyne triple bonds and deprotecting to form a multihydroxyl terminated multi-branched all alkyl polymer.

U.S. Pat. No. 5,206,410 relates the compound 4-[1-(2-cyanoethyl)]-4-[1-(3-(4-chlorobenzyloxy))propyl]-bis-1,7-(4-chloro benzyloxy)heptane. This compound is used as a synthon for the preparation of unimolecular micelles.

U.S. Pat. No. 5,788,989 relates a composition comprising at least one dendrimer and at least one active substance occluded in this dendrimer, wherein the dendrimer has terminal groups, and wherein a sufficient number of terminal groups are blocked with blocking agents whereby active subtances are occluded within dendrimers.

The prior art appears to be silent with regard to the formation of a UPM having an ionizable core for enhanced functionality in a variety of pharmaceutical applications.

SUMMARY OF THE INVENTION

The present invention describes the preparation of UPM that bear a hydrophilic shell and a potentially ionizable and relatively hydrophobic core at a determined pH value. The core becomes electrostatically charged as the pH is changed. Such micelles can be made from either biodegradable or non-biodegradable polymers. Loaded drugs can be physically retained in the micelles when the pH of the surrounding medium favors interactions with the core. Upon a change in pH, modification in the ionization state of the core will decrease the interactions between the drug and the inner core and promote the release of the micellar contents. For instance, hydrophobic drugs will be loaded in these micelles under conditions where the core is uncharged. Upon protonation or deprotonation of the core, the increase in polarity will provide the driving force to release the compound.

Accordingly, it is an objective of the instant invention to teach a unimolecular polymeric micelle composition having an ionizable core.

It is yet another objective of the instant invention to provide a process for the controlled release of pharmacological compositions from unimolecular polymeric micelles, wherein said release is triggered by altering the ionization state of the micelle core.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
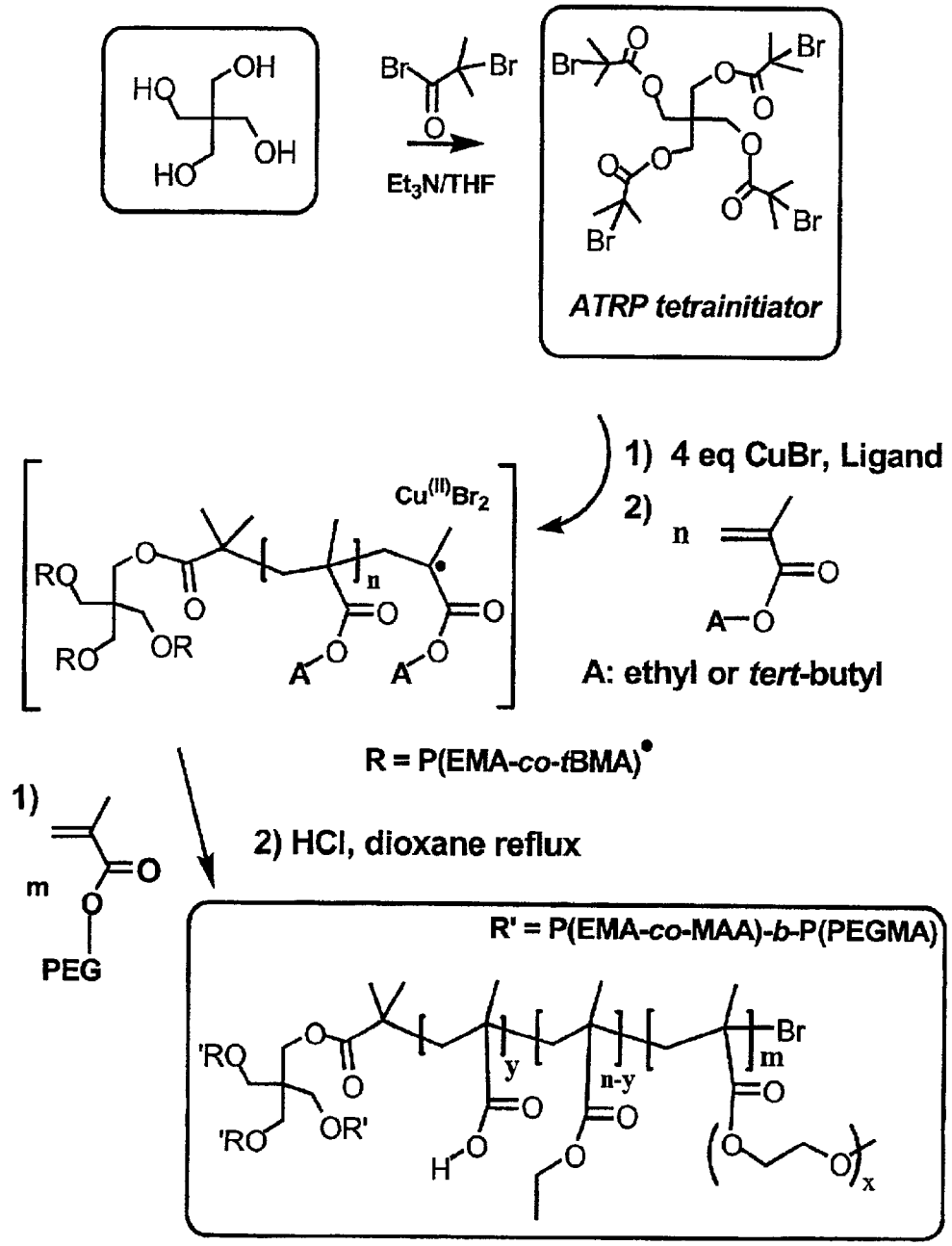
FIG. 1 presents the synthesis scheme of a UPM, with an ionizable and hydrophobized inner core, and a non-ionic hydrophilic outer shell.

Now referring to FIG. 1, a step-wise analysis of a process for synthesizing a unimolecular polymeric micelle having a hydrophobic inner core and a hydrophilic corona is illustrated.

Without intending to be limited to a particular synthesis procedure, UPM are most preferably prepared by atom transfer radical polymerization (ATRP). However, any alternative procedure such as other living radical polymerizations or condensation of preformed functionalized polymers could also be used.

UPM can be prepared by a divergent approach (see Ranger et al. 28*th Int. Symposium on Controlled Release of Bioactive Materials* (2001), CRS Meetings, in press) or convergent approach (see Frechet et al. U.S. Pat. No. 5,041,516; Bosman et al. Polym. Prep. (2001), ACS Meetings, in press). The divergent approach utilizes a multifunctionalized initiator to polymerize the molecular arms of the UPM. In this case, the hydrophobic core is synthesized first followed by the hydrophilic shell. The convergent approach consists, first in synthesizing an amphiphilic diblock copolymer starting with the hydrophilic block and, then, cross-linking the extremity of the hydrophobic block using a small amount of cross-linking agent.

For purposes of illustration, only the divergent approach will be herein described to prepare the pH-sensitive UPM.

The radical initiator for the synthesis of the polymer by ATRP can be a di-, tri-, tetra-, penta- or hexafunctionalized molecule. This multifunctionalized molecule initiates the polymerization of multiple chains, giving multiarm-shape or star-shape polymers. For example, the radical initiator can be synthesized from pentaerythritol, tris(hydroxymethane) ethane or tris(hydroxymethane)-aminomethane (TRIS). The initiator bears a halogeno functionality that can be activated for ATRP. Without intending to be limited to any particular substituent, this functionality can include at least one of 2-halogenoisobutyrylate derivatives, 2-halogenopropionate derivatives, 2-halogenoacetate derivatives or 1-(halogenomethyl)benzene derivatives.

The catalyst for the ATRP consists of a metallic salt and a ligand. Non-limiting examples of suitable salts may include one or more compounds selected from copper(I) bromide, copper(I) chloride or copper(I) thiocyanate, iron (II) and nickel(0 or I) compounds. Illustrative, but non-limiting examples of the ligand may include 2,2'-bipyridine derivatives or bis(dimethylamino) compounds (e.g. N,N,N',N',N'',N''-pentamethyldiethylene-triamine (PMDETA)).

In general, the UPM are synthesized from vinyl monomers, vinyl oligomers or eventually vinyl polymers. These monomers/oligomers/polymers can be acrylate, acrylamide, alkylacrylate, alkylacrylamide, arylacrylate and arylacrylamide derivatives for which the alkyl and aryl terms stand for aliphatic or aromatic moieties, respectively (e.g. methacrylate, methacrylamide derivatives, vinylterminated poly(lactide) or vinyl-terminated poly($\epsilon$-caprolactone), etc). Moreover, N-vinylpyrrolidone derivatives, vinylacetate derivatives, allylamine and styrene derivatives can also be considered for the preparation of the pH-responsive UPM.

More specifically, the inner core is prepared by polymerizing ionizable (containing basic or acidic units) monomers alone or in combination with hydrophobic vinyl compounds. The ionizable monomers could be alkylacrylic acid derivatives, (aminoalkyl) acrylate or (aminoalkyl) alkylacrylate derivatives. The acidic or basic units of the polymer chain can be derived from a non-ionizable precursor (e.g. tert-butylmethacrylate). The hydrophobic vinyl compounds could be acrylate, acrylamide, alkylacrylate, alkylacrylamide arylacrylate and arylacrylamide derivatives for which the alkyl and aryl terms stand for aliphatic or aromatic moieties, respectively (e.g. methacrylate, methacrylamide derivatives, vinylterminated poly(lactide) or vinyl-terminated poly($\epsilon$-caprolactone), etc).

The outer shell is obtained from the polymerization of hydrophilic vinyl compounds once the synthesis of the inner core is completed. Non-limiting examples of useful hydrophilic vinyl compounds can be (2-hydroxypropyl) methacrylamide (HPMA), N-vinyl-2-pyrrolidone, vinylterminated poly(ethylene glycol), N-isopropylacrylamide and their related derivatives.

UPM, that are not intended to be administered parenterally, should have molecular weights not exceeding 40,000 when they are not biodegradable. There is no restriction on molecular weights for biodegradable UPM or non-biodegradable UPM, which are, used either orally or locally as long as the UPM remain soluble in water.

Pharmacological constituents useful in the pharmaceutical formulations of the present invention include, but are not limited to, various therapeutic agents, drugs, peptides, proteins, genetic material (e.g. oligonucleotides), genetically altered constituents, polyionic constituents and the like.

These constituents may be inserted within the unimolecular micelle according to techniques well known to one skilled in the art. For example, drugs can be incorporated into the polymeric micelle compositions of the invention by physical entrapment through dialysis, emulsification techniques, simple equilibration of the drug and micelles in an aqueous medium or solubilization of a drug/polymer solid dispersion in water.

Micelles can be targeted to specific cells or tissues via the inclusion of targeting ligands, e.g. monoclonal antibodies, lectins, sugars, vitamins, peptides or immunologically distinct fragments thereof or the like moieties which provide the micelles with an ability to preferentially concentrate in a particular target area.

Therapeutic agents which may be used are any compounds which can be entrapped, in a stable manner, in polymeric micelles and administered at a therapeutically effective dose. Preferably, the therapeutic agents used in accordance with the invention are hydrophobic or polyionic (e.g. DNA). Although not wishing to be limited to any particular agent, suitable drugs may include antitumor compounds such as phthalocyanines (e.g. aluminum chloride phthalocyanine), anthracyclines (e.g. doxorubicin), poorly soluble antimetabolites (e.g. methotrexate, mitomycin, 5-fluorouracil) and alkylating agents (e.g. carmustine). Micelles may also contain taxanes such as paclitaxel.

Additional drugs which may also be contained in micelles are conventional hydrophobic antibiotics and antifungal agents such as amphotericin B and itraconazole, poorly water-soluble immunomodulators such as cyclosporin, poorly water-soluble antiviral drugs such as HIV protease inhibitors and poorly water-soluble steroidal (e.g. dexamethasone), and non-steroidal (e.g. indomethacin) anti-inflammatory drugs.

For the purpose of the present invention, hydrophobic drugs are loaded in the inner core under conditions where the latter is completely or mostly uncharged. Permanently charged or ionizable drugs are loaded in the inner core under conditions where the latter is completely or mostly charged.

The following examples are illustrative of the preparation of ionizable core-bearing unimolecular polymeric micelles of varying molecular weights (from alternatively useful precursor materials).

EXAMPLES

Synthesis of star-poly([poly(ethylene glycol)]methacrylate)-block-poly(ethyl methacrylate-co-tert-butyl methacrylate) and star-poly([poly(ethylene glycol)]methacrylate)-block-poly(ethyl methacrylate-co-methacrylic acid).

Star-P(PEGMA200)-b-P(EMA$_{50}$-co-tBMA$_{50}$) (precursor #1)

Star-P(PEGMA200)-b-P(EMA$_{50}$-co-MMA$_{50}$) (from precursor #1)

Star-P (PEGMA1000)-b-P(EMA$_{50}$-co-tBMA$_{50}$) (precursor #3).

Star-P(PEGMA1000)-b-P(EMA$_{50}$-co-MAA$_{50}$) (from the precursor #3)

In accordance with the methodology of the present invention, the following terms are set forth:

The term star means that these polymers are in fact molecules having a central emerging point linked to many linear or branched polymeric arms.

The term following the word star describes the shell or the corona of the UPM.

The number attached to the term PEGMA represents the molecular weight of the PEG chain included in the repeating unit (or in the monomer).

The subscript text indicates the ratio in a polymeric segment.

The letter b indicates that polymers and/or polymeric arms are based on a diblock copolymeric structure.

The last term following the letter b describes the core of UPM.

Materials:

All products were purchased from Aldrich (Milwaukee, Wis.). Copper(I) bromide (99.99% Grade), 2-bromoisobutyryl bromide, anhydrous triethylamine and N,N,N',N',N'',N''-pentamethyldiethylenetriamine (PMDETA) were used without further purification. Ethyl methacrylate (EMA), tert-butyl methacrylate (tBMA) and methylPEG methacrylate (M$_n$ of PEG segment: 200 and 1000) (PEGMA200 and PEGMA1000 respectively) were used as vinyl monomers. Prior to use, tetrahydrofuran (THF) was distilled over sodium, using benzophenone as drying indicator.

Synthesis of ATRP Tetrainitiator:

Tetra(2-Bromoisobutyryl) Pentaerythritolate:

To a solution of pentaerythritol (10 g, 0.005 mol) and triethylamine (3.0 g, 0.03 mol) in 140 mL of anhydrous THF, slightly cooled in a water-ice bath, was slowly added 2-bromoisobutyryl bromide (17.2 mL, 0.14 mol). The solution was then warmed to room temperature and stirred for 24 h. The mixture was poured into water and extracted with methylene chloride. The organic extracts were washed successively with a HCl 1M and NaOH 1M solution (containing NaCl), and dried over magnesium sulfate. The solvent was removed under reduced pressure. The product was recrystallized in ethanol/diethyl ether. The title compound was recovered by simple filtration, following a washing with diethyl ether. Yield: 97% after precipitation. Light brownish crystal.

$^1$H NMR (δ, ppm, CDCl$_3$): 4.33 (s, 8H); 1.94 (s, 24H).

Figure 2:
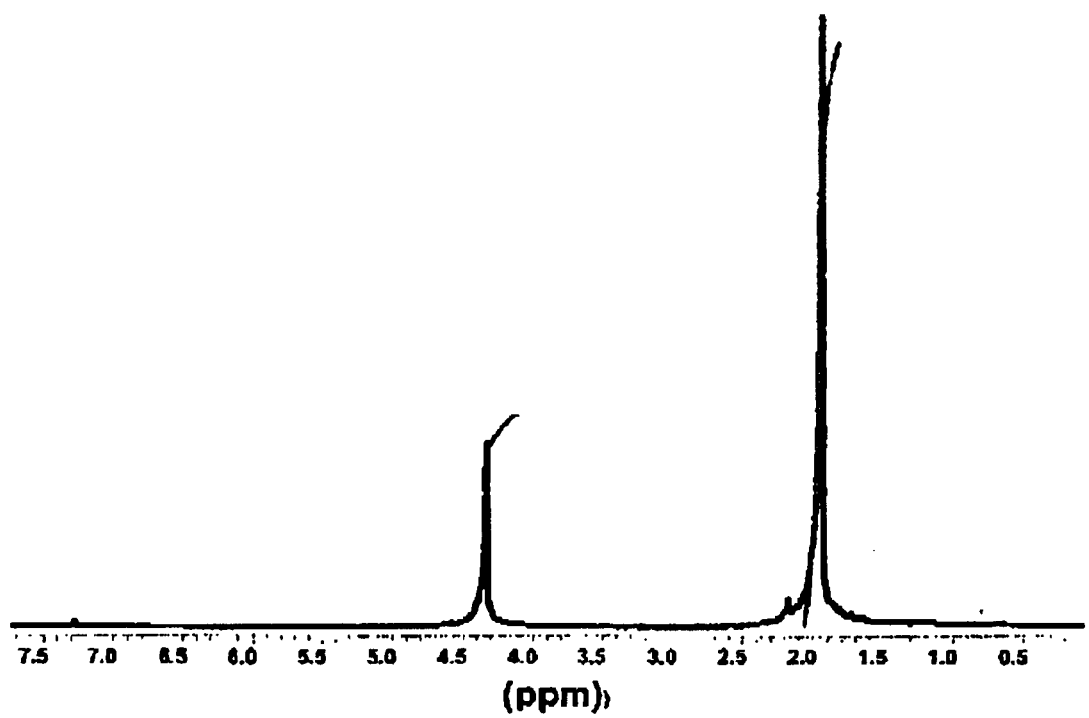
FIG. 2 presents the $^1$H NMR spectrum of the tetrainitiator of the atom transfer radical polymerization (ATRP)

Referring to FIG. 2, a $^1$H NMR spectrum of the ATRP tetrainitiator is set forth. This radical initiator is very stable in presence of air or water.

ATRP for Star-P(PEGMA1000)-b-P(EMA$_{50}$-co-tBMA$_{50}$):

The ATRP two-step polymerization of monomers was carried out in solution, using tetra(2-bromoisobutyryl) pentaerythritolate. The ATRP tetrainitiator (1 eq.) was added to a solution containing PMDETA (4.1 eq.), Cu(I)Br (4.1 eq.), EMA (16 eq.) and tBMA (16 eq.) in THF (0.35 M). The mixture was degassed with argon for 15–20 min at room temperature and was then heated to 60° C. overnight. Then, the mixture was transferred in a flask containing an excess of the PEGMA (M$_n$: 1000, 32 eq.), previously degassed with successive cycles of vacuum/argon. The reaction pot was stirred at 60° C. for 48 h. After the polymerization, the mixture was poured in THF, containing 10% of ethanol. The resulting polymers were filtered on silica gel, with THF as eluent, to remove copper bromide. Finally, polymers were dialyzed (Spectra/Por no.1, MW cutoff 50,000) against water during 48 h and then freeze-dried. Yield: 50–65%.

ATRP for Star-P(PEGMA200)-b-P(EMA$_{50}$-co-tBMA$_{50}$)

The ATRP two-step polymerization of monomers was also carried out in solution, using tetra(2-bromoisobutyryl) pentaerythritolate. The ATRP tetrainitiator (1 eq.) was added to a solution containing PMDETA (3 eq.), Cu(I)Br (2 eq.), EMA (16 eq.) and TBMA (16 eq.) in THF (0.35 M). The mixture was degassed with argon for 15–20 min at room temperature and was then heated to 65° C. during 1 h. Then, PEGMA (M$_n$: 200, 40 eq.), previously degassed with argon, was transferred to the mixture. The reaction pot was stirred at 65° C. for 5 h. After the polymerization, the mixture was poured in THF, containing 10% of ethanol. The resulting polymers were filtered on silica gel, with THF as eluent, to remove copper bromide. Finally, polymers were dialyzed (Spectra/Por no.1, MW cutoff 6,000–8,000) against water during 48 h and then freeze-dried. Yield: 65–75%.

Transformation of tBMA Into MAA:

This transformation of ester groups, bearing a tert-butyl, into carboxylic acid consisted in a hydrolysis in acidic conditions. To a solution of the polymers having tBMA units (7.7 mmol) in dioxane (2.6 M) was added concentrated HCl (32 mmol) for 5 h. The methacrylic acid derivatives were precipitated in diethyl ether and filtered. The polymers were dissolved in ethanol, dialyzed against water and freeze dried.

Analytical Methods:

$^1$H and $^{13}$C NMR spectra were recorded on a Bruker AMX300 and ARX400 in deuterated chloroform (CDCl$_3$) and methanol (CD$_3$OD) (CDN Isotopes, Canada) at 25° C. Number-(M$_n$) and weight-average (M$_W$) molecular weight were determined by size exclusion chromatography (SEC) with an Alliance GPVC2000 (Waters, Milford, Mass.) and by nuclear magnetic resonance spectroscopy ($^1$H-NMR).

Referring now to FIG. 3, $^1$H NMR spectra of non-ionic star-P (PEGMA1000)-b-P (EMA$_{50}$-co-tBMA$_{50}$) (A) and ionizable star-P(PEGMA1000)-b-P(EMA$_{50}$-co-MMA$_{50}$)(B) star-shape copolymers are illustrated.

Figure 3A:
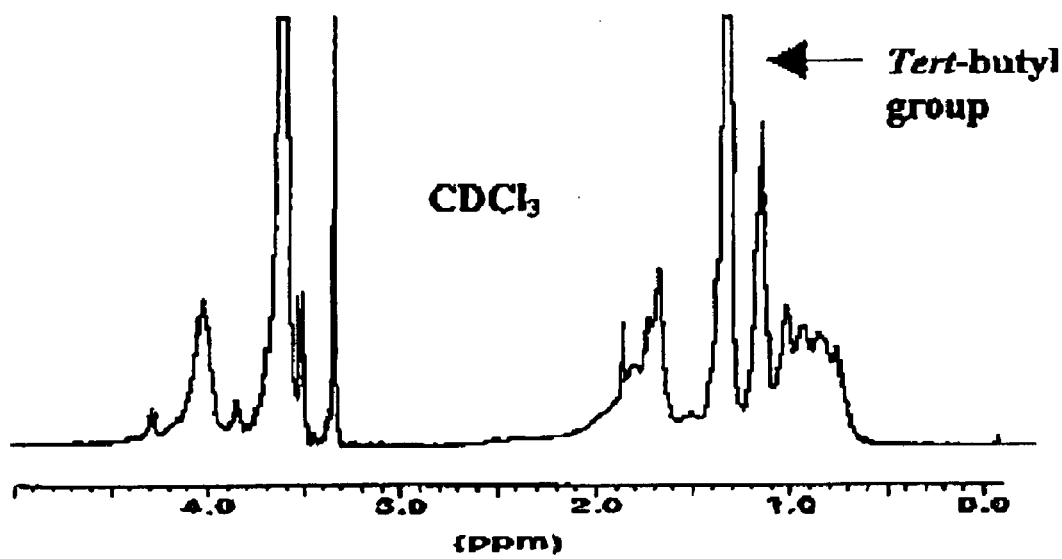
FIG. 3A is the $^1$H NMR spectra of the non-ionic star-P (PEGMA1000)-b-P (EmA$_{50}$-co-tBMA$_{50}$)

FIG. 3A shows the $^1$H NMR spectrum of the star-(PEGMA1000)-b-P(EMA$_{50}$-co-tBMA$_{50}$), which is the precursor of the PMAA derivative. The $^1$H NMR analysis of a fraction collected before the reaction with PEGMA revealed that each arm of the hydrophobic core had 4 units of EMA and 4 units of tBMA. The molecular weight (M$_n$) of the core and shell were 4800 and 4400, respectively. When the polymerization was stopped, the PEGMA1000-based UPM possessed a M$_n$ of about 9000 (evaluated by $^1$H NMR analysis).

Star-P(PEGMA200)-b-P(EMA$_{50}$-co-tBMA$_{50}$) leads to higher yields of synthesis by the use of shorter PEG chain incorporated in monomers. By SEC analysis, the core of star-P(PEGMA200)-b-P(EMA$_{50}$-co-tBMA$_{50}$) has molecular weights (M$_n$) of about 2800 with a polydispersity of about 1.2. After the incorporation of PEGMA units, these UPM are highly water-soluble and show M$_n$ of 11800.

The acidic cleavage of the tBMA groups leads to (star-P (PEGMA1000)-b-P(EMA$_{50}$-co-MAA$_{50}$)), giving the ionizable units of the inner core required for the pH-controlled release properties.

Figure 3B:
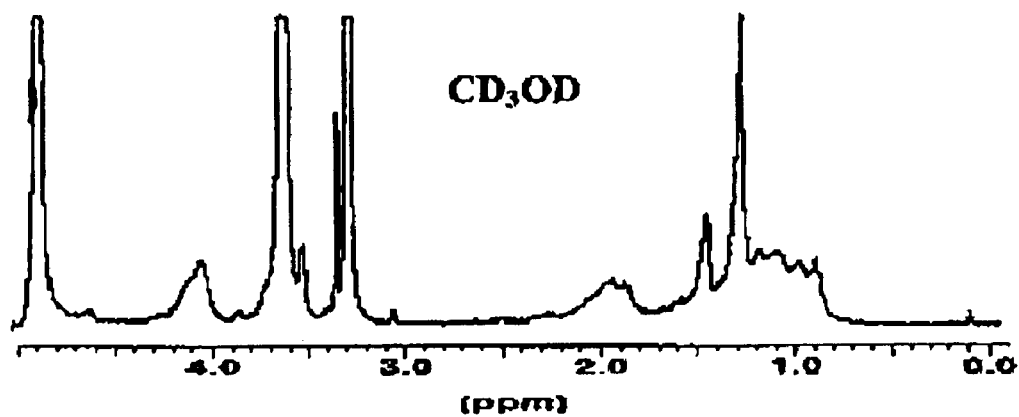
FIG. 3B is the $^1$H NMR spectra of the ionizable star-P (PEGMA1000)-b-P (EMA$_{50}$-co-MAA$_{50}$)
Figure 4A:
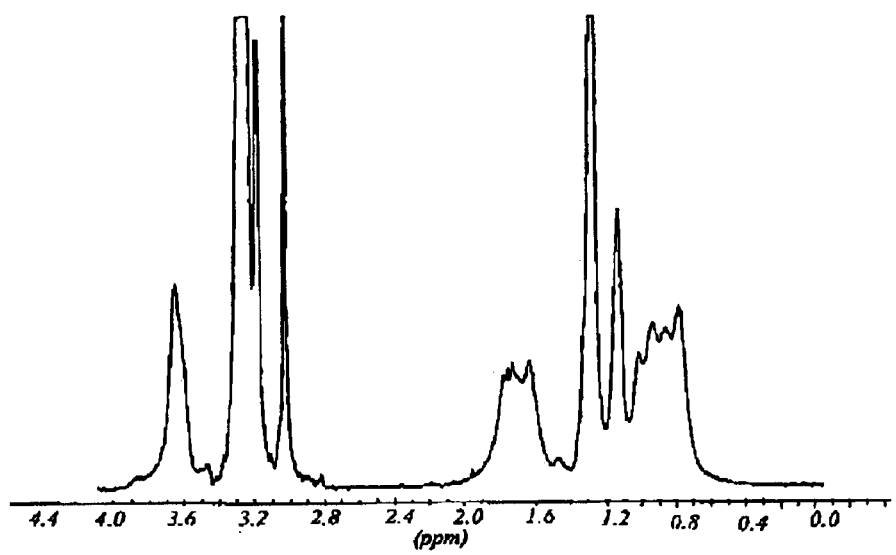
FIG. 4A is the $^1$H NMR spectra of the non-ionic star-P (PEGMA200)-b-P (EmA$_{50}$-co-tBMA$_{50}$)
Figure 4B:
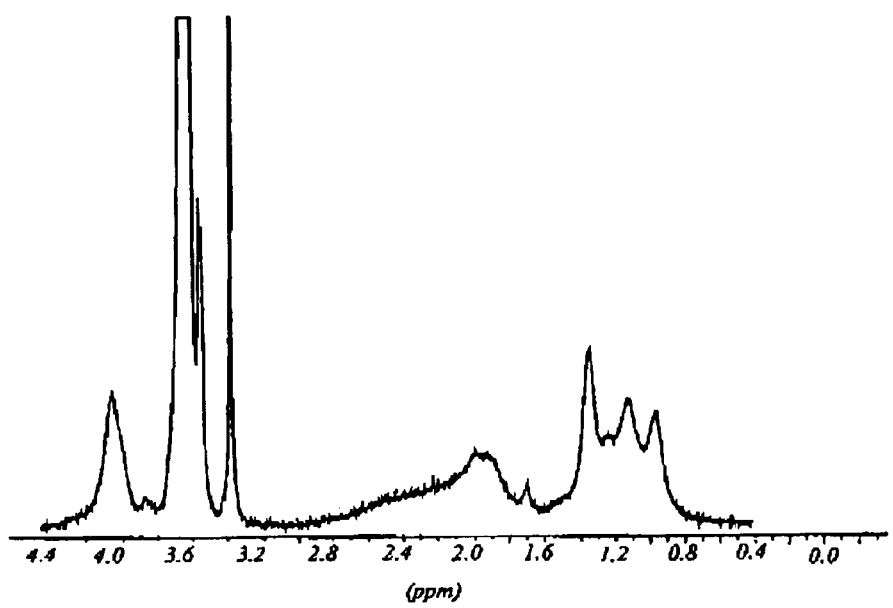
FIG. 4B is the $^1$H NMR spectra of the ionizable star-P (PEGMA200)-b-P (EMA$_{50}$-co-MAA$_{50}$).

As shown in FIG. 3B, at least 70% of the tBMA units were cleaved. In the case of star-P(PEGMA200)-b-P(EMA$_{50}$-co-tBMA$_{50}$), the hydrolysis of tBMA units into carboxylic acid groups is practically quantitative (FIG. 4).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

One skilled in the art will readily appreciate that the present invention is well adapted to carry out the objects and obtain the ends and advantages mentioned, as well as those inherent therein. The compounds, compositions, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A unimolecular polymeric micelle comprising an ionizable inner core and a hydrophilic outer shell wherein said ionizable inner core includes ionizable repeating units alone or in combination with non-ionic hydrophobic repeating units and wherein said ionizable repeating units include at least one compound selected from the group consisting of alkylacrylic acid derivatives, acrylic acid derivatives (aminoalkyl) acrylate derivatives, and (aminoalkyl) alkylacrylate derivatives and wherein said non-ionic hydrophobic repeating units include at least one compound selected from the group consisting of acrylate derivatives, acrylamide derivatives, alkylacrylate derivatives, alkylacrylamide derivatives, arylacrylate derivatives and arylacrylamide derivatives; and wherein said hydrophilic outer shell is non-ionic and originates from functionalized and hydrophilic polymers, and includes at least one hydrophilic compound selected from the group consisting of vinyl monomers a vinyl oligomers and vinyl polymers.

2. The unimoleoular polymeric micelle in accordance with claim 1 wherein:

said alkylacrylate derivatives and alkylacrylamide derivatives include at least one aliphatic moiety selected from the group consisting of methacrylate derivatives and methacrylamide derivatives.

3. The unimolecular polymeric micelle of claim 1 wherein:

said hydrophilic compound includes at least one compound selected from the group consisting of acrylate derivatives, acrylamide derivatives, alkylacrylate derivatives, alkylacrylamide derivatives, and N-vinyl-2-pyrrolidone derivatives.

4. The unimolecular polymeric micelle of claim 1 wherein:

said functionalized and hydrophilic polymers are selected from the group consisting of poly(ethylene glycol) or poly (N-vinyl-2-pyrrolidone).

5. A pharmaceutical formulation comprising the unimolecular polymeric micelle of claim 1 in combination with an effective amount of at least one pharmacological constituent.

6. The pharmaceutical formulation of claim 5 wherein said pharmacological constituent is released from the micelle in response to a change of pH.

7. The pharmaceutical formulation of claim 5 where the pharmacological constituent is a drug.

8. The pharmaceutical formulation of claim 5 where the pharmacological constituent is a peptide, protein or genetic material.

9. The pharmaceutical formulation of claim 5 including a suitable targeting ligand.

* * * * *